United States Patent
Zhang et al.

(10) Patent No.: US 7,786,164 B2
(45) Date of Patent: Aug. 31, 2010

(54) LIPOPHILIC DI(ANTICANCER DRUG) COMPOUNDS, COMPOSITIONS, AND RELATED METHODS

(75) Inventors: Yuehua Zhang, Bothell, WA (US); Lynn C. Gold, Seattle, WA (US)

(73) Assignee: Sonus Pharmaceuticals, Inc., Bothell, WA (US)

( * ) Notice: Subject to any disclaimer, the term of this patent is extended or adjusted under 35 U.S.C. 154(b) by 924 days.

(21) Appl. No.: 11/612,769

(22) Filed: Dec. 19, 2006

(65) Prior Publication Data

US 2007/0141093 A1  Jun. 21, 2007

Related U.S. Application Data

(60) Provisional application No. 60/752,769, filed on Dec. 20, 2005.

(51) Int. Cl.
*A61K 31/337* (2006.01)
*C07D 407/12* (2006.01)

(52) U.S. Cl. .................................... 514/449; 549/510
(58) Field of Classification Search ................ 514/449; 549/510
See application file for complete search history.

(56) References Cited

FOREIGN PATENT DOCUMENTS

| GB | 2 056 973 A | 3/1981 |
|---|---|---|
| WO | 96/38138 A1 | 12/1996 |
| WO | 96/39143 A1 | 12/1996 |
| WO | 00/10988 A1 | 3/2000 |
| WO | 03/095460 A1 | 11/2003 |

*Primary Examiner*—Charanjit S Aulakh
(74) *Attorney, Agent, or Firm*—Christensen O'Connor Johnson Kindness PLLC (57) ABSTRACT

Lipophilic di(anticancer drug) compounds, compositions that include the compounds, and methods for treating a cell proliferative disease using the compounds.

9 Claims, 6 Drawing Sheets

LIPOPHILIC DI(ANTICANCER DRUG) COMPOUNDS, COMPOSITIONS, AND RELATED METHODS

CROSS-REFERENCE TO RELATED APPLICATION

This application claims the benefit of U.S. Provisional Application No. 60/752,769, filed Dec. 20, 2005, which application is incorporated herein by reference in its entirety.

BACKGROUND OF THE INVENTION

The ability to administer biologically effective drugs that are poorly soluble in biocompatible solvents to mammals has been a major hurdle in the realm of pharmaceutical and medicinal chemistry. In particular, difficulties arise when an active drug is either insoluble in water or unstable in other biocompatible solvents. Solubility problems are common and often cause delays in drug development. Several technologies have been developed to facilitate the delivery of poorly soluble and insoluble compounds. Examples of technologies specifically designed to solve solubility problems include complexing agents, nanoparticles, microemulsions, solubility enhancing formulations, prodrugs and water soluble prodrugs, and novel polymer systems.

One way to improve the solubility of medicinal agents is to chemically modify them or conjugate them to another molecule to alter the solubility profile in a particular solvent. Conjugates of active drugs, often referred to as prodrugs, include a chemical derivative of a biologically-active parent compound. Prodrugs may be biologically inert or maintain activity that is substantially less than the parent or active compound. The parent compound is released from the prodrug in vivo by a variety of mechanisms, including, for example, hydrolysis or enzymatic cleavage. The rate of release is influenced by several factors, including the type of chemical bond joining the active parent drug to the conjugate moiety.

There continues to be a need for new methods, which are both safe and effective, of solubilizing and delivering poorly soluble active drug molecules.

SUMMARY OF THE INVENTION

In one aspect, the present invention provides lipophilic di(anticancer drug) compounds that have been modified to increase their lipophilicity. The compounds of the invention include two anticancer drug moieties and a lipophilic linker moiety. The anticancer drug moieties are covalently coupled to the lipophilic linker to form a lipophilic di(anticancer drug) compound. Methods for making the lipophilic di(anticancer drug) compounds are also provided.

In one embodiment, the lipophilic di(anticancer drug) compound has the formula:

D-A-R'-A'-D wherein,
D is an anticancer drug moiety;
R' is a moiety selected from the group consisting of:
(a) substituted and unsubstituted alkyl,
(b) substituted and unsubstituted branched alkyl,
(c) substituted and unsubstituted heteroalkyl,
(d) substituted and unsubstituted cycloalkyl,
(e) substituted and unsubstituted alkenyl,
(f) substituted and unsubstituted alkynyl,
(g) substituted and unsubstituted aryl, and
(h) substituted and unsubstituted aralkyl;

A and A' are independently selected from the group consisting of:
(a) —S(=O)—,
(b) —SO$_2$—,
(c) —SO(NR$_1$)—
(d) —C(=O)—
(e) —C(=O)O—,
(f) —C(=O)NR$_1$—,
(g) —C(=O)OC(=O)—,
(h) —C(=O)OC(=O)O—,
(i) —P(=O)(OR$_1$)O—,
(j) —P(=O)(NR)O—,
(k) —SO$_{20}$—,
(l) —S(=O)NR$_1$—,
(m) —SO$_2$NR$_1$—,
(n) —O—, and
(o) —NHR$_1$—, wherein R$_1$ is selected from hydrogen, C$_{1-6}$ n-alkyl, C$_{3-12}$ branched alkyl, substituted or unsubstituted C$_{3-6}$ cycloalkyl, substituted or unsubstituted aryl, and substituted or unsubstituted aralkyl.

In another aspect of the invention, compositions that include the compounds of the invention are provided. In one embodiment, the composition includes a compound of the invention, optionally one or more other therapeutic agents, and a lipophilic medium. Methods for making the compositions are also provided.

In a further aspect, the invention provides emulsion and micelle formulations that include a compound of the invention. The emulsion formulations include an oil phase and an aqueous phase. The emulsion may be an oil-in-water emulsion or a water-in-oil emulsion. The micelle formulation includes a compound of the invention and an aqueous phase. Methods for making the emulsion and micelle formulations are also provided.

In other aspects, methods for administering the compounds of the invention to a subject in need thereof, and methods for treating a condition treatable by administration of a compound of the invention are also provided.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE INVENTION

In one aspect, the present invention provides anticancer drug compounds that have been modified to increase their lipophilicity. The compounds of the invention are lipophilic di(anticancer drug) compounds. The compounds of the invention include two anticancer drug moieties and a lipophilic linker moiety. The lipophilic linker moiety is a bifunctional moiety. The anticancer drug moieties are covalently coupled to the lipophilic linker moiety to provide a lipophilic di(anticancer drug) compound. Methods for making the lipophilic di(anticancer drug) compounds are provided.

In another aspect of the invention, compositions that include one or more of the modified anticancer drug compounds of the invention are provided. In one embodiment, the composition includes a lipophilic medium. Methods for making the compositions are also provided.

In a further aspect, the invention provides emulsions that include one or more of the modified anticancer drug compounds. In one embodiment, the emulsion includes a modified anticancer drug compound, a lipophilic medium in which the modified anticancer drug compound is soluble, and an aqueous medium. The emulsion may be an oil-in-water emulsion or a water-in-oil emulsion. In one embodiment, the lipophilic medium is a tocopherol. Methods for making the modified anticancer drug compound-containing emulsions are also provided.

In another aspect, the invention provides micelle formulations that include one or more of the modified anticancer drug compounds. In one embodiment, the micelle formulation includes a modified anticancer drug compound, one or more solvents in which the modified anticancer drug compound is soluble, one or more surfactants, and an aqueous medium.

In one embodiment, a lipophilic anticancer drug compounds of the invention is represented by formula:

D-R-D in which R is a lipophilic linker moiety and D is an anticancer drug moiety.

As used herein, the term "lipophilic linker moiety," refers to a bifunctional group which covalently links two anticancer drug moieties to form the lipophilic di(anticancer drug) compound of the invention. The linker moiety has the following formula:

A-R'-A' wherein R' is a bivalent radical and independently selected from substituted or unsubstituted alkylene, substituted or unsubstituted heteroalkylene, substituted or unsubstituted branched alkylene, substituted or unsubstituted cycloalkylene, substituted or unsubstituted alkynylene, substituted or unsubstituted alkenylene, substituted or unsubstituted arylene, substituted or unsubstituted aralkylene, or any combination of aforementioned groups;

wherein A and A', functional groups, are independently selected from the group consisting of
(a) —S(=O)—,
(b) —SO$_2$—,
(c) —SO(NR$_1$)—
(d) —C(=O)—
(e) —C(=O)O—,
(f) —C(=O)NR$_1$—,
(g) —C(=O)OC(=O)—,
(h) —C(=O)OC(=O)O—,
(i) —P(=O)(OR$_1$)O—,
(j) —P(=O)(NR)O—,
(k) —SO$_{20}$—,
(l) —S(=O)NR$_1$—, and
(m) —SO$_2$NR$_1$—,
(n) —O—,
(o) —NHR$_1$—, wherein R$_1$ is selected from H, C$_{1-6}$ n-alkyl, C$_{3-12}$ branched alkyl, substituted or unsubstituted C$_{3-6}$ cycloalkyl, substituted or unsubstituted aryl, and substituted or unsubstituted aralkyl.

As used herein, the term "alkyl" refers to straight chain and branched alkyl groups, typically having from 1 to 20 carbon atoms. Cycloalkyl groups include monocyclic and polycyclic alkyl groups, monocyclic alkyl groups typically having from about 3 to about 8 carbon atoms in the ring.

The term "aryl" refers to monocyclic and polycyclic aromatic compounds having from 6 to 14 carbon or hetero atoms, and includes carbocyclic aryl groups and heterocyclic aryl groups. Representative aryl groups include phenyl, naphthyl, pyridinyl, pyrimidinyl, thiazolyl, indolyl, imidazolyl, furanyl, and the like. As used herein, the term "aryl" includes heteroaryl groups. The term "aralkyl" refers to an alkyl group that is substituted with an aryl group.

The term "acyl" refers to a —C(=O)R group, where R is a substituted or unsubstituted alkyl, substituted or unsubstituted cycloalkyl, substituted or unsubstituted heteroalkyl, substituted or unsubstituted aryl, substituted or unsubstituted heteroaryl, or substituted or unsubstituted aralkyl group.

The term "substituted" refers to a substituent in which one or more hydrogen atoms is replaced with another group such as, for example, alkyl, cycloalkyl, heteroalkyl, aryl, heteroaryl, halogen, hydroxy, amino, thio, and alkoxy.

As used herein, the term "anticancer drug moiety" refers to an anticancer drug that can be covalently coupled to a bifunctional lipophilic linker moiety to provide a lipophilic di(anticancer drug) compound of the invention. Anticancer drugs that may be used in the invention have one or more functional groups, or may be modified to include one or more functional groups, for covalent coupling to the lipohilic linker. Anticancer drug compounds selected for conjugation need not be substantially water-insoluble, although the lipophilic di(anticancer drug) compounds of the present invention are especially well suited for formulating and delivering such water-insoluble compounds. The lipophilic di(anticancer drug) compounds of the invention provide for the solubilization of anticancer drug compounds in pharmaceutical formulations that would be otherwise difficult to formulate for administration.

Representative anticancer drugs useful in making the lipophilic di(anticancer drug) compounds of the invention include camptothecin and its derivatives, e.g. 10-hydroxycamptothecin, 7-ethyl-10-hydroxycamptothecin (SN38), 9-aminocamptothecin, 9-amino-7-ethylcamptothecin, 10-aminocamptothecin, 10-amino-7-ethylcamptothecin, paclitaxel and its derivatives, docetaxel and its derivatives, and other taxanes and taxane derivatives.

In one embodiment, D (camptothecin moiety) has the formula wherein R is selected from the group consisting of H and CH₂CH₃, and X is selected from the group consisting of O and NH.

In one embodiment, D (camptothecin moiety) has the formula wherein R is selected from the group consisting of H and CH₂CH₃, and X is selected from the group consisting of O and NH.

In one embodiment, D (camptothecin moiety) has the formula wherein R is selected from the group consisting of H and CH₂CH₃.

In one embodiment, D (camptothecin moiety) has the formula wherein R is selected from the group consisting of H and CH₂CH₃; X is selected from the group consisting of O and NH; and $R_2$ is selected from the group consisting of H, acyl, alkyl, branched alkyl, substituted or unsubstituted cycloalkyl, substituted or unsubstituted aryl, and substituted or unsubstituted aralkyl.

In one embodiment, D (camptothecin moiety) has the formula wherein R is selected from the group consisting of H and CH₂CH₃; X is selected from the group consisting of O and NH; $R_2$ is selected from the group consisting of H, acyl, alkyl, branched alkyl, substituted or unsubstituted cycloalkyl, substituted or unsubstituted aryl, and substituted or unsubstituted aralkyl.

In one embodiment, D (paclitaxel moiety) has the formula

In one embodiment, D (docetaxel moiety) has the formula

In another aspect of the invention, methods for making lipophilic di(anticancer drug) compounds are provided. A bifunctional lipophilic linker moiety can be covalently coupled to two anticancer drug compounds to form a lipophilic di(anticancer drug) compound.

Figure 1:
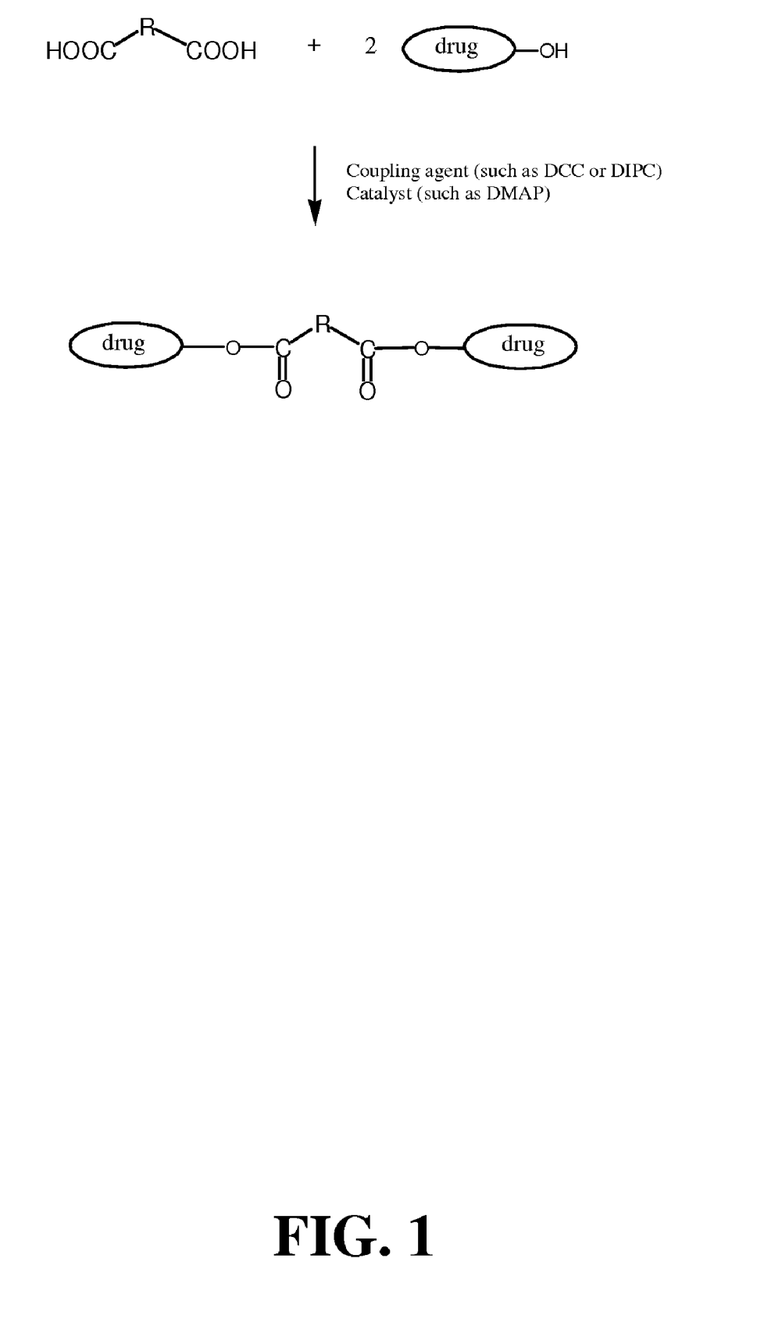
FIG. 1 schematically illustrates the reaction of a lipophilic dicarboxylic acid and anticancer drug compounds containing a hydroxyl group to provide a lipophilic di(anticancer drug) compound.

In a representative embodiment, two carboxyl groups of a lipophilic molecule are directly coupled with two hydroxyl groups of two anticancer drug compounds to form a lipophilic di(anticancer drug) compound. Such a method is illustrated schematically in FIG. 1. In FIG. 1, R is a lipophilic bivalent moiety independently selected from n-alkylene, branched alkylene, substituted alkylene, cycloalkylene or substituted cycloalkylene, arylene or substituted arylene, aralkyl or substituted aralkylene.

In another embodiment, a lipophilic molecule containing a hydroxyl group or an amino group may be functionalized with a reagent, for example, 2-chloroacetic acid, succinic acid anhydride, phthalic acid anhydride, isophthalic acid, terephthalic acid, epichlorohydrin, phosphorous oxychloride, alkyl dichlorophosphate, aryl dichlorophosphate, alkyl phosphonic dichloride, aryl phosphonic dichloride, chlorosulfonic acid, or 4-isocyanatobenzoyl chloride (but not limited to). The functional group added to the lipophilic molecule may be, for example, a carboxyl group (—COOH), oxiranyl group (—CH(O)CH$_2$), phosphoric chloride group (—P(O)ORCl), phosphonic chloride group (—P(O)RCl), chlorosulfonic group (—SO$_2$Cl), isocyanato group (—N=C=O), carbonyl chloride group (—COCl). The resulting carboxyl group, oxiranyl group, isocyanato group, or acid chloride group can then be reacted with two anticancer drugs or functionalized anticancer drugs to provide a lipophilic di(anticancer drug) compound.

Figure 2:
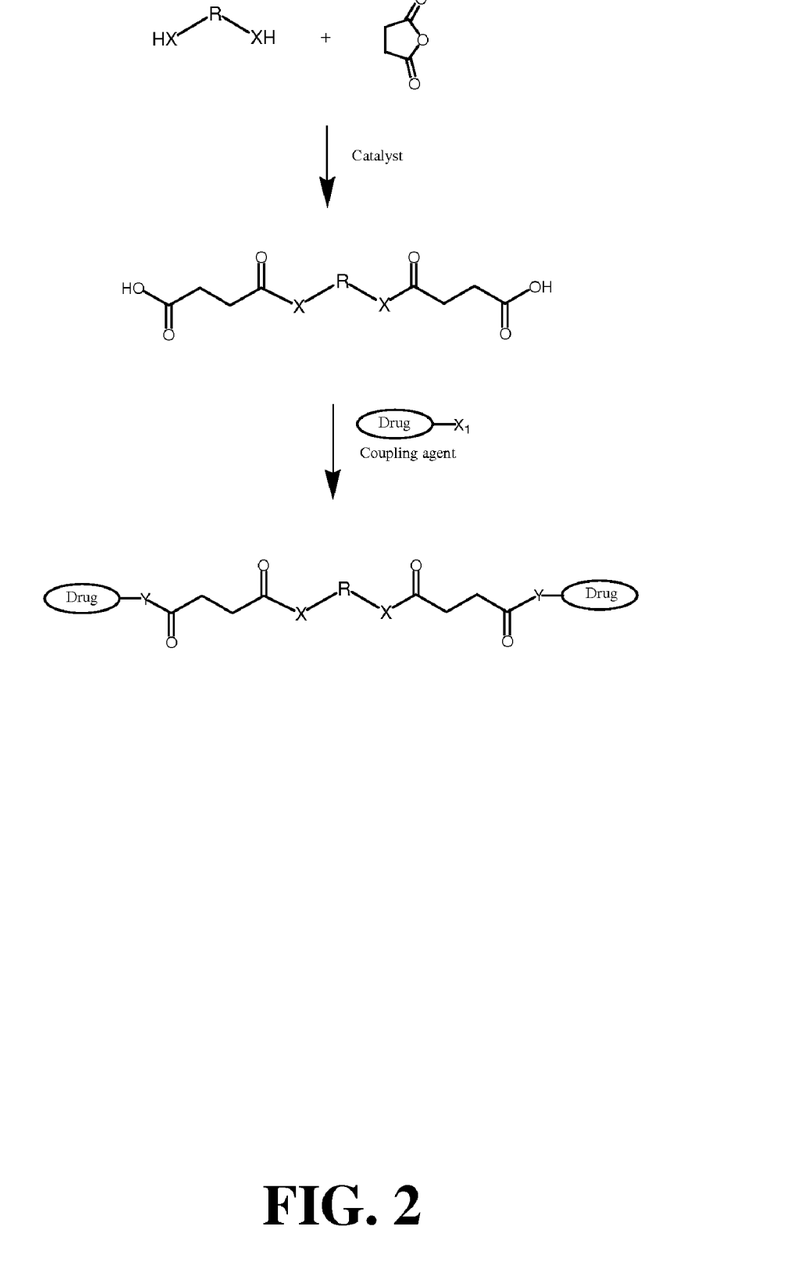
FIG. 2 schematically illustrates functionalization of a lipophilic compound with a carboxyl group (—COOH), and reaction of the resulting acid with appropriately functionalized anticancer drug compounds to provide a lipophilic di(anticancer drug) compound; X is an oxygen atom, or NR$_1$ group; X$_1$ is a hydroxyl group, carboxyl group, mercapto or thiol group, or an amino group; Y is an oxygen atom, a sulfur atom, a NH, a NR$_2$; R$_1$ and R$_2$ are independently selected from H, C$_{1-6}$ n-alkyl, C$_{3-12}$ branched alkyl, substituted or unsubstituted C$_{3-6}$ cycloalkyl, substituted or unsubstituted aryl, substituted or unsubstituted aralkyl.

In a representative embodiment, a lipophilic molecule containing two hydroxyl or amino groups is reacted with succinic acid anhydride to form a disuccinic acid which is coupled with the hydroxyl, amine, or carboxyl group of two anticancer drugs to form a lipophilic di(anticancer drug) compound. Such a method is illustrated schematically in FIG. 2. In FIG. 2, representative X groups may be an O atom, or NR$_1$ group; X$_1$ may be OH, NH$_2$, NHR, SH, or CO$_2$H; representative Y groups include O, NH, NHR$_2$, S, and C(=O)O; and R$_1$ and R$_2$ are independently selected from n-alkyl, branched alkyl, substituted alkyl, cycloalkyl or substituted cycloalkyl, aryl or substituted aryl, aralkyl or substituted aralkyl.

The syntheses of representative lipophilic di(anticancer drug) compounds of the invention are illustrated in FIGS. 3-6 and described in Examples 1 to 4.

Figure 3:
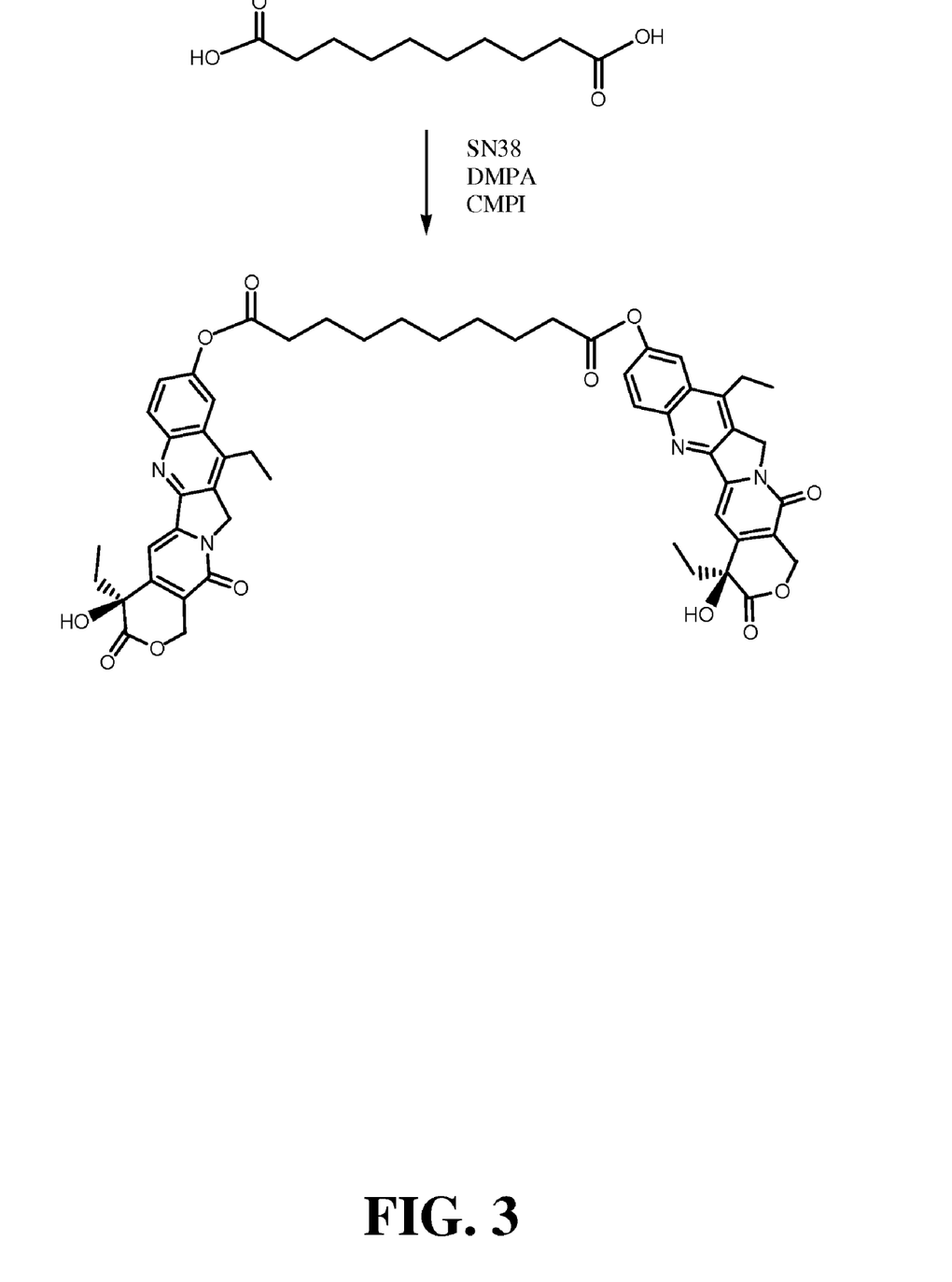
FIG. 3 schematically illustrates preparation of sebacate bis(7-ethylcamptothecin-10-yl)ester.

FIG. 3 illustrates the preparation of sebacate bis(7-ethylcamptothecin-10-yl)ester. As used herein, sebacate bis(7-ethylcamptothecin-10-yl)ester refers to decanedioic acid bis [(4S)-4,11-diethyl-3,4,12,14-tetrahydro-4-hydroxy-3,14-dioxo-1H-pyrano[3',4':6,7]indolizino[1,2-b]quinolin-9-yl] ester. Two free carboxyl groups of sebacic acid are coupled to the hydroxyl group at C-10 of two 7-ethyl-10-hydroxycamptothecin (SN38) molecules in the presence of 2-chloro-1-methylpyridinium iodide and 4-(dimethylamino)pyridine to form sebacate bis(7-ethylcamptothecin-10-yl)ester. The preparation of sebacate bis(7-ethylcamptothecin-10-yl)ester is described in Example 1.

Figure 4:
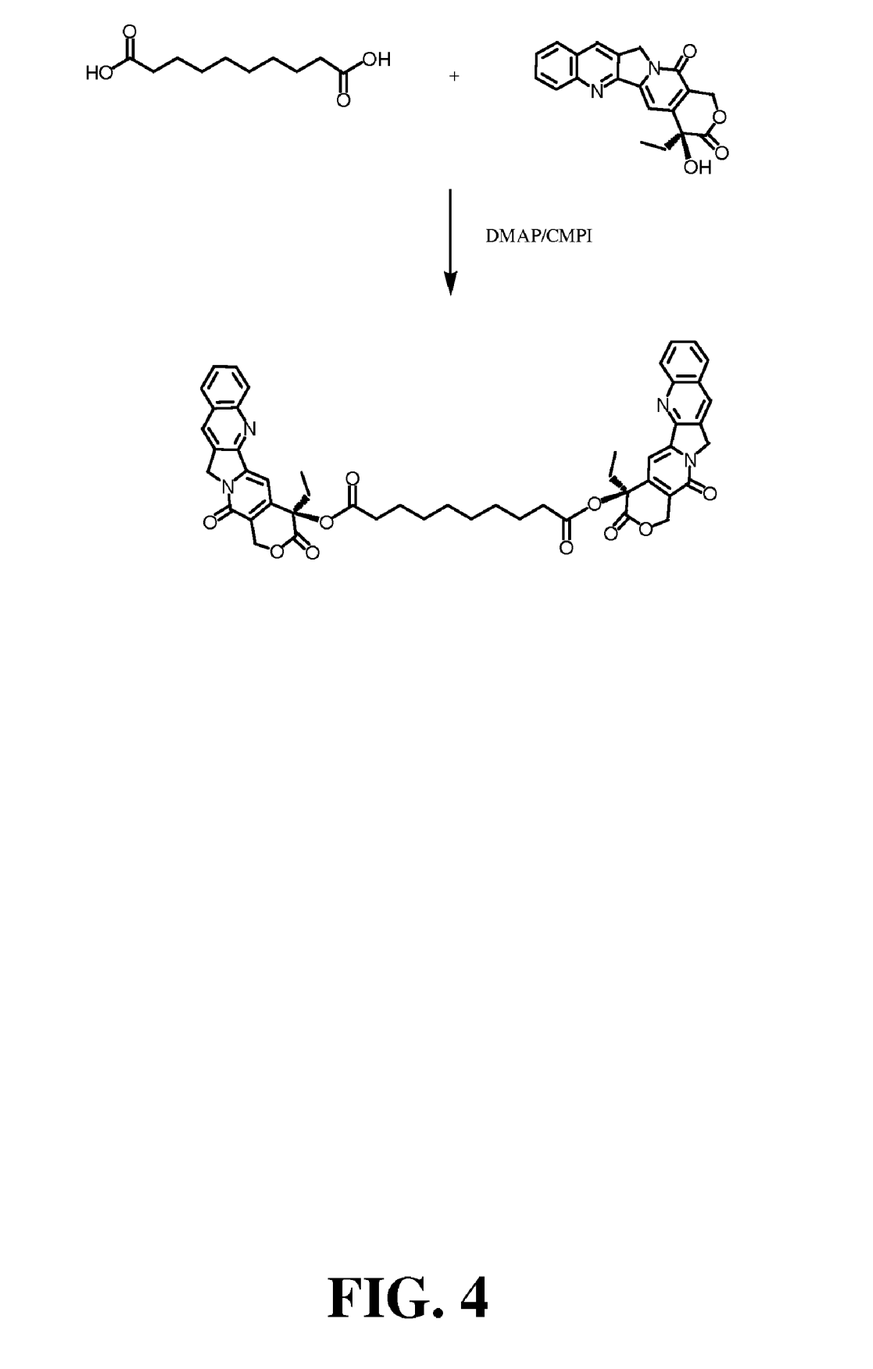
FIG. 4 schematically illustrates preparation of sebacate bis(camptothecin-20-yl)ester.

FIG. 4 illustrates the preparation of sebacate bis(camptothecin-20-yl)ester. As used herein, sebacate bis(camptothecin-20-yl)ester refers to decanedioic acid bis[(4S)-4-ethyl-3,4,12,14-tetrahydro-3,14-dioxo-1H-pyrano[3',4':6,7]indolizino [1,2-b]quinolin-4-yl]ester. Two free carboxyl groups of sebacic acid are coupled to the hydroxyl group at C-20 of two camptothecin molecules in the presence of 2-chloro-1-methylpyridinium iodide and 4-(dimethylamino)pyridine to form sebacate bis(camptothecin-20-yl)ester. The preparation of sebacate bis(camptothecin-20-yl)ester is described in Example 2.

Figure 5:
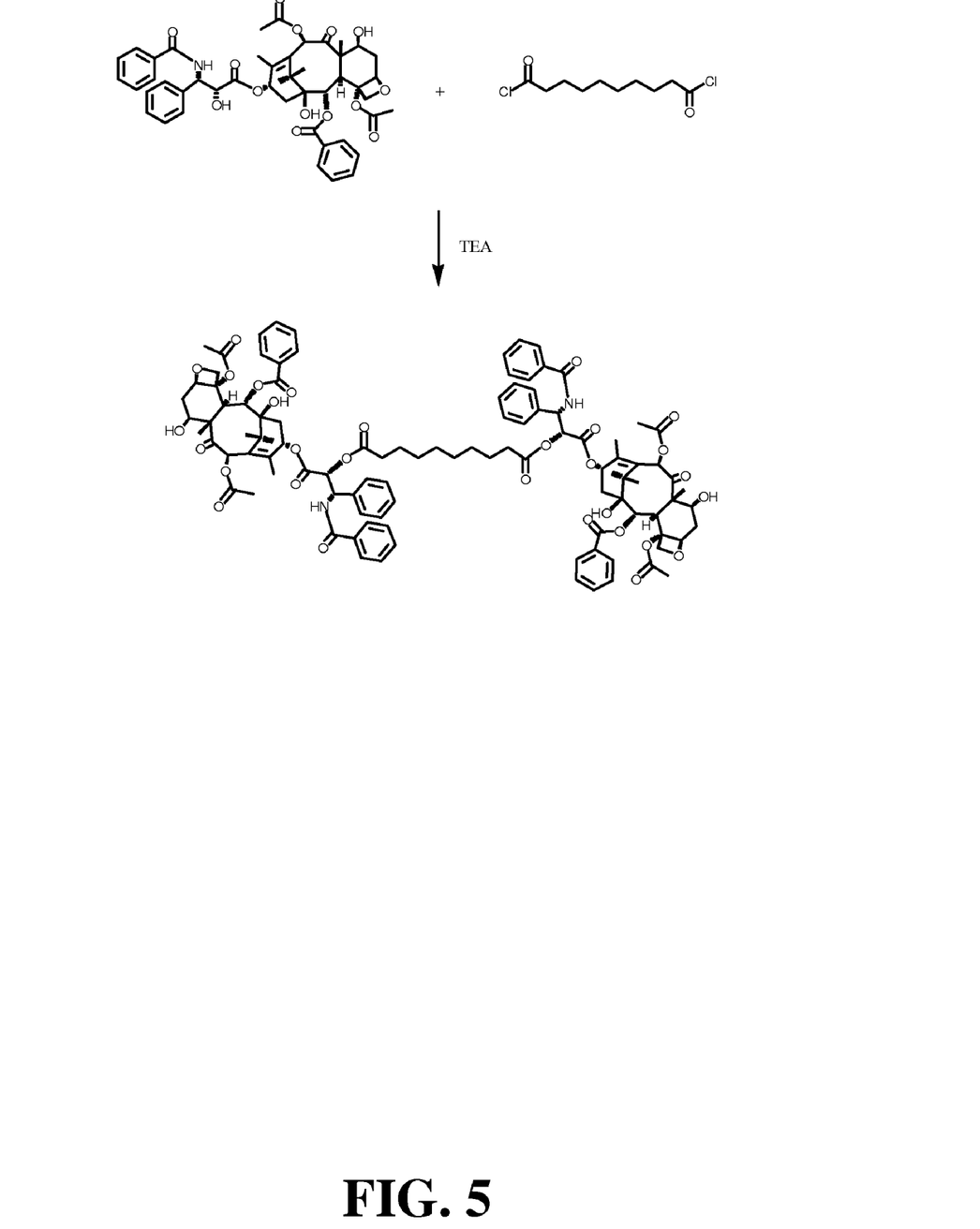
FIG. 5 schematically illustrates preparation of sebacate bis(paclitaxel-2'-yl)ester.

FIG. 5 illustrates the preparation of sebacate bis(paclitaxel-2'-yl)ester. As used herein, sebacate bis(paclitaxel-2'-yl)ester refers to decanedioic acid bis[(1R,2S)-2-(benzoylamino)-1-[[[(2aR,4S,4aS,6R,9S,11S,12S,12aR,12bS)-6,12b-bis (acetyloxy)-12-(benzoyloxy)-2a,3,4,4a,5,6,9,10,11,12,12a, 12b-dodecahydro-4,11-dihydroxy-4a,8,13,13-tetramethyl-5-oxo-7,11-methano-1H-cyclodeca[3,4]benz[1,2-b]oxet-9-yl]oxy]carbonyl]-2-phenylethyl]ester. Two carbonyl chloride groups of sebacoyl chloride are coupled with hydroxyl group at side chain of two paclitaxel molecules in the presence of triethylamine to form sebacate bis(paclitaxel-2'-yl)ester. The preparation of sebacate bis(paclitaxel-2'-yl)ester is described in Example 3.

Figure 6:
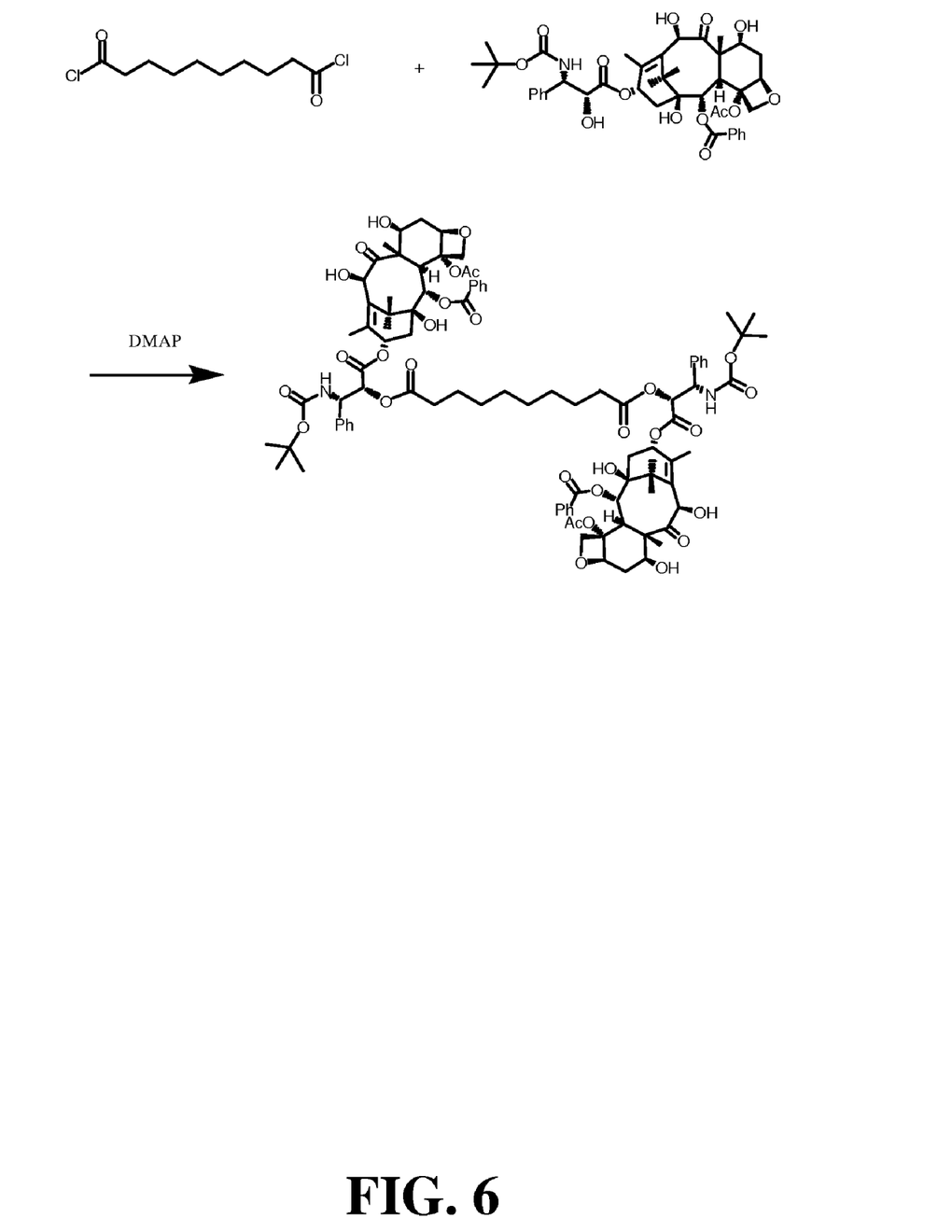
FIG. 6 schematically illustrates preparation of sebacate bis(docetaxel-2'-yl)ester.

FIG. 6 illustrates the preparation of sebacate bis(docetaxel-2'-yl)ester. As used herein, sebacate bis(docetaxel-2'-yl)ester refers to decanedioic acid bis[(1R,2S)-1-[[[(2aR,4S,4aS,6R, 9S,11S,12S,12aR,12bS)-12b-(acetyloxy)-12-(benzoyloxy)-2a,3,4,4a,5,6,9,10,11,12,12a,12b-dodecahydro-4,6,11-trihydroxy-4a,8,13,13-tetramethyl-5-oxo-7,11-methano-1H-cyclodeca[3,4]benz[1,2-b]oxet-9-yl]oxy]carbonyl]-2-[[(1,1-dimethylethoxy)carbonyl]amino]-2-phenylethyl]ester. A sebacoyl chloride molecule reacts with two docetaxel molecule in the presence of 4-(dimethylamino)pyridine to form sebacate bis(docetaxel-2'-yl)ester. The preparation of sebacate bis(docetaxel-2'-yl)ester is described in Example 4.

In another aspect, the present invention provides compositions that include the compounds of the invention. The compositions include one or more compounds of the invention, optionally one or more additional therapeutic agents, and a lipophilic medium.

In one embodiment, a lipophilic di(anticancer drug) compound is dissolved in the lipophilic medium.

In one embodiment, the lipophilic medium includes a tocopherol (e.g., α-tocopherol). As used herein, the term "tocopherol" refers to a family of natural or synthetic compounds, also known by their generic names, tocol or vitamin E. In addition to tocopherol compounds, tocotrienol compounds are included in this family. Tocol compounds have a phenolic alcohol (C-6) chroman head and a phytyl tail (C-2). Tocopherols constitute a series of related benzopyranols (or methyl tocols) in which the C-2 phytyl (sixteen carbon) side chain is saturated. Representative tocopherols include α-tocopherol, (d-form, dl-form, 1-form), β-tocopherol (d-form, dl-form, 1-form), γ-tocopherol (d-form, dl-form, 1-form), and δ-tocopherol (d-form, dl-form, 1-form). Tocotrienols are similar in structure to tocopherols except that the trienols have three double bonds in the C-2 phytyl side chain. Representative tocotrienols include α-tocotrienol, (d-form, dl-form, 1-form), β-tocotrienol (d-form, dl-form, 1-form), γ-tocotrienol (d-form, dl-form, 1-form), and δ-tocotrienol (d-form, dl-form, 1-form).

The lipophilic medium (or carrier) of the composition can be any one of a variety of lipophilic mediums including, for example, oils. Representative oils useful as the lipophilic medium include the following:

fatty acids and esters thereof, including carboxylic acids of various chain lengths, mostly straight chain, but which could be branched, examples of which include capric, caprylic, caproic, lauric, myristic, stearic, oleic, linoleic, behenic, and as well as saturated or unsaturated fatty acids and esters;

fatty acids esterified with glycerin to form mono-, di-, or triglycerides, which can be synthetic or derived from natural sources, including, but not limited to, for example, glycerides such as soybean oil, cottonseed oil, rapeseed oil, fish oil, castor oil, Capmul MCM, Captex 300, Miglyol 812, glyceryl monooleate, triacetin, acetylated monoglyceride, tristearin, glyceryl behenate, and diacetyl tartaric acid esters of monoglycerides;

glycerides conjugated to other moieties, such as polyethylene glycol (for example, Labrasol, Labrafac, Cremophor EL);

phospholipids, either natural or synthetic, such as dimyristoyl phosphatidylcholine, egg lecithin, and pegylated phospholipids;

other fatty esters including fatty alcohols (myristyl myristate, isopropyl palmitate), or sugars (sorbitan monooleate, SPAN 80, Tween 80, sucrose laurate);

fatty alcohols such as stearyl alcohol, lauryl alcohol, benzyl alcohol, or esters or ethers thereof, such as benzyl benzoate; and fat-soluble vitamins and derivatives, for example, vitamin E (including all of the tocopherols and tocotrienols, and tocopherol and tocotrienol derivatives, such as vitamin E succinate, vitamin E acetate, and vitamin E succinate polyethylene glycol (TPGS)).

Organic co-solvents can also be used in the compositions, optionally in combination with water, including for example, ethanol, polyethylene glycol, propylene glycol, glycerol, N-methylpyrrolidone, and dimethyl sulfoxide.

In a further aspect, the invention provides emulsion, microemulsion, and micelle formulations that include a compound of the invention. Methods for making the emulsions, microemulsions, and micelle formulations are also provided. As used herein, the term "emulsion" refers to a colloidal dispersion of two immiscible liquids, such as an oil and water, in the form of droplets, whose diameter, in general, are between 0.1 and 3.0 microns and that is typically optically opaque, unless the dispersed and continuous phases are refractive index matched. Such systems possess a finite stability, generally defined by the application or relevant reference system, which may be enhanced by the addition of amphiphilic molecules or viscosity enhancers.

The term "microemulsion" refers to a thermodynamically stable isotropically clear dispersion of two immiscible liquids, such as an oil and water, stabilized by an interfacial film of surfactant molecules. A microemulsion has a mean droplet diameter of less than 200 nm, in general between 10-50 nm.

The emulsion and microemulsion formulations include an oil phase and an aqueous phase. The emulsion or microemulsion can be an oil-in-water emulsion or a water-in-oil emulsion.

In the absence of water, mixtures of oil(s) and non-ionic surfactant(s) form clear and isotropic solutions that are known as self-emulsifying drug delivery systems (SEDDS) and can be used to improve lipophilic drug dissolution and oral absorption.

In one embodiment, the compound is present in the formulation in an amount from about 0.005 to about 3.0 weight percent based on the total weight of the formulation. In one embodiment, the compound is present in the formulation in an amount from about 0.01 to about 2.5 weight percent based on the total weight of the formulation. In one embodiment, the compound is present in the formulation in an amount from about 0.1 to about 1.5 weight percent based on the total weight of the formulation.

In one embodiment, the lipophilic medium is present in the formulation in an amount from about 2 to about 20 weight percent based on the total weight of the formulation. In one embodiment, the lipophilic medium is present in the formulation in an amount from about 4 to about 12 weight percent based on the total weight of the formulation. In one embodiment, the lipophilic medium is present in the formulation in an amount from about 6 to about 10 weight percent based on the total weight of the formulation.

In one embodiment of the emulsion or microemulsion, the lipophilic medium includes a tocopherol, and the aqueous medium is water.

In addition to the compounds of the invention, the emulsion or microemulsion formulations can include other components commonly used in emulsions and microemulsions, and, in particular, components that are used in pharmaceutical emulsions and microemulsions. These components include, for example, surfactants and co-solvents. Representative surfactants include nonionic surfactants such as surface active tocopherol derivatives and surface active polymers.

Suitable surface active tocopherol derivatives include tocopherol polyethylene glycol derivatives, such as vitamin E succinate polyethylene glycol (e.g., d-α-tocopherol polyethylene glycol 1000 succinate, TPGS), which is a vitamin E derivative in which a polyethylene glycol is attached by a succinic acid ester at the hydroxyl of vitamin E. The tocopherol polyethylene glycol derivative includes a polyethylene glycol. Suitable tocopherol polyethylene glycol derivatives include polyethylene glycol having a variety of molecular weights (e.g., 200, 300, 400, 600, 1000, or more). As used herein, "vitamin E succinate polyethylene glycol" includes vitamin E succinate polyethylene glycol and derivatives of vitamin E polyethylene glycol having various ester and ether links. TPGS is a non-ionic surfactant (HLB=16-18). Surface active tocopherol derivatives (e.g., TPGS) can be present in the formulations of the invention in an amount from about 1 to about 10 weight percent, about 2 to about 6 weight percent, or about 5 weight percent, based on the total weight of the formulation.

Suitable nonionic surfactants include block copolymers of ethylene oxide and propylene oxide known as POLOXAMERS or PLURONICS. These synthetic block copolymers of having the general structure: $H(OCH_2CH_2)_a(OC_3H_6)_b(OCH_2CH_2)_aOH$. The following variants based on the values of a and b are commercially available from BASF Performance Chemicals (Parsippany, N.J.) under the trade name PLURONIC and consist of the group of surfactants designated by the CTFA name of POLOXAMER 108, 188, 217, 237, 238, 288, 338, 407, 101, 105, 122, 123, 124, 181, 182, 183, 184, 212, 231, 282, 331, 401, 402, 185, 215, 234, 235, 284, 333, 334, 335, and 403. For the most commonly used POLOXAMERS 124, 188, 237, 338, and 407 the values of a and b are 12/20, 79/28, 64/37, 141/44 and 101/56, respectively. In one embodiment the nonionic surfactant is present in the formulation in an amount from about 0.5 to about 5 weight percent based on the total weight of the formulation.

Co-solvents useful in the formulations include ethanol, polyethylene glycol, propylene glycol, glycerol, N-methylpyrrolidone, and dimethylsulfoxide, among others. Polyethylene glycol (PEG) is a hydrophilic, polymerized form of ethylene glycol, consisting of repeating units having the chemical structure: $(-CH_2CH_2O-)$. The general formula for polyethylene glycol is $H(OCH_2CH_2)_nOH$. The molecular weight ranges from 200 to 10,000. Such various forms are described by their molecular weights, for example, PEG-200, PEG-300, PEG-400, and the like.

In a further aspect, the invention provides micelle formulations that include a compound of the invention, one or more surfactants, one or more solvents, and an aqueous phase. Micelles are organized aggregates of one or more surfactants in solution. In one embodiment, the compound is present in the formulation in an amount from about 0.005 to about 3.0 weight percent based on the total weight of the formulation. In one embodiment, the compound is present in the formulation in an amount from about 0.01 to about 2.5 weight percent based on the total weight of the formulation. In one embodiment, the compound is present in the formulation in an amount from about 0.1 to about 1.0 weight percent based on the total weight of the formulation. Suitable surfactants include those noted above, and in the amounts noted above. In one embodiment of the micelle formulation, the surfactant is tocopherol polyethylene glycol succinate (TPGS).

The micelle formulation can also include additional components such as solvents and co-solvents, including those noted above. In one embodiment, the micelle formulation includes a polyethylene glycol and a lower alkyl alcohol (e.g., ethanol). In one embodiment, the solvents and co-solvents are present in an amount from about 2 to about 20 weight percent based on the total weight of the formulation. The micelle, emulsion, and microemulsion formulations include an aqueous phase. In one embodiment, the aqueous phase includes deionized water. In another embodiment, the aqueous phase includes saline. In another embodiment, the aqueous phase is saline buffered with an organic acid (e.g., succinate, citrate).

The invention also provides the use of the compounds of the invention in the manufacture of a medicament. For example, for compounds of the invention that include a anticancer drug moiety derived from a anticancer drug compound effective in treating cell proliferative disease, the invention provides the use of such compounds in the manufacture of a medicament for the treatment of cell proliferative disease.

In other aspects, methods for administering a compound of the invention to a subject in need thereof, and methods for treating a condition treatable by administration of a therapeutically effective amount of a compound of the invention are also provided. These methods include the administration of the compounds, compositions, emulsion formulations, microemulsion formulations, and micelle formulations described herein.

In one embodiment, the invention provides a method for treating a condition that is treatable by the parent, unmodified anticancer drug compound (e.g., a cell proliferative disease such as cancer). In the method, a therapeutically effective amount of a compound of the invention is administered to a subject in need thereof.

In one embodiment, the invention provides a method for treating a cell proliferative disease by administering a compound of the invention having a anticancer drug moiety derived from a anticancer drug effective in treating cell proliferative disease. Representative cell proliferative diseases treatable by the compounds of the invention include hematologic cancers, such as leukemia, lymphoma, and myeloma; and nonhematologic cancers, such as solid tumor carcinomas (e.g., breast, ovarian, pancreatic, colon, colorectal, non-small cell lung, and bladder), sarcomas, and gliomas.

Therapeutically effective amounts of the compounds will generally range up to the maximally tolerated dosage, but the concentrations are not critical and may vary widely. The precise amounts employed by the attending physician will vary, of course, depending on the compound, route of administration, physical condition of the patient and other factors. The daily dosage may be administered as a single dosage or may be divided into multiple doses for administration.

The amount of the compound actually administered will be a therapeutically effective amount, which term is used herein to denote the amount needed to produce a substantial beneficial effect. Effective doses may be extrapolated from dose-response curves derived from in vitro or animal model test systems. The animal model is also typically used to determine a desirable dosage range and route of administration. Such information can then be used to determine useful doses and routes for administration in humans or other mammals. The determination of an effective dose is well within the capability of those skilled in the art. Thus, the amount actually administered will be dependent upon the individual to which treatment is to be applied, and will preferably be an optimized amount such that the desired effect is achieved without significant side-effects.

Therapeutic efficacy and possible toxicity of the compounds of the invention can be determined by standard pharmaceutical procedures, in cell cultures or experimental animals (e.g., $ED_{50}$, the dose therapeutically effective in 50% of the population; and $LD_{50}$, the dose lethal to 50% of the population). The dose ratio between therapeutic and toxic effects is the therapeutic index, and it can be expressed as the ratio $LD_{50}$ to $ED_{50}$. Modified anticancer drug compounds that exhibit large therapeutic indices are particularly suitable in the practice of the methods of the invention. The data obtained from cell culture assays and animal studies may be used in formulating a range of dosage for use in humans or other mammals. The dosage of such compounds lies preferably within a range of circulating concentrations that include the $ED_{50}$ with little or no toxicity. The dosage typically varies within this range depending upon the dosage form employed, sensitivity of the patient, and the route of administration. Thus, optimal amounts will vary with the method of administration, and will generally be in accordance with the amounts of conventional medicaments administered in the same or a similar form.

The compounds of the invention can be administered alone, or in combination with one or more additional therapeutic agents. For example, in the treatment of cancer, the compounds can be administered in combination with therapeutic agents including, but not limited to, androgen inhibitors, such as flutamide and luprolide; antiestrogens, such as tamoxifen; antimetabolites and cytotoxic agents, such as daunorubicin, fluorouracil, floxuridine, interferon alpha, methotrexate, plicamycin, mercaptopurine, thioguanine, adriamycin, carmustine, lomustine, cytarabine, cyclophosphamide, doxorubicin, estramustine, altretamine, hydroxyurea, ifosfamide, procarbazine, mutamycin, busulfan, mitoxantrone, carboplatin, cisplatin, streptozocin, bleomycin, dactinomycin, and idamycin; hormones, such as medroxyprogesterone, estramustine, ethinyl estradiol, estradiol, leuprolide, megestrol, ocreotide, diethylstilbestrol, chlorotrianisene, etoposide, podophyllotoxin, and goserelin; nitrogen mustard derivatives, such as melphalan, chlorambucil, mechlorethamine, and thiotepa, steroids, such as betamethasone; and other antineoplastic agents, such as live *Mycobacterium bovis*, dicarbazine, asparaginase, leucovorin, mitotane, vincristine, vinblastine, and taxotere. Appropriate amounts in each case will vary with the particular agent, and will be either readily known to those skilled in the art or readily determinable by routine experimentation.

Administration of the compounds of the invention is accomplished by any effective route, for example, parenteral, topical, or oral routes. Methods of administration include inhalational, buccal, intramedullary, intravenous, intranasal, intrarectal, intraocular, intraabdominal, intraarterial, intraarticular, intracapsular, intracervical, intracranial, intraductal, intradural, intralesional, intramuscular, intralumbar, intramural, intraocular, intraoperative, intraparietal, intraperitoneal, intrapleural, intrapulmonary, intraspinal, intrathoracic, intratracheal, intratympanic, intrauterine, intravascular, and intraventricular administration, and other conventional means. The compounds of the invention having anti-tumor activity can be injected directly into a tumor, into the vicinity of a tumor, or into a blood vessel that supplies blood to the tumor.

The emulsion, microemulsion, and micelle formulations of the invention can be nebulized using suitable aerosol propellants that are known in the art for pulmonary delivery of the compounds.

The compounds of the invention may be formulated into a composition that additionally comprises suitable pharmaceutically acceptable carriers, including excipients and other compounds that facilitate administration of the compound to a subject. Further details on techniques for formulation and administration may be found in the latest edition of "Remington's Pharmaceutical Sciences" (Maack Publishing Co., Easton, Pa.).

Compositions for oral administration may be formulated using pharmaceutically acceptable carriers well known in the art, in dosages suitable for oral administration. Such carriers enable the compositions containing the compounds of the invention to be formulated as tablets, pills, dragees, capsules, liquids, gels, syrups, slurries, suspensions, suitable for ingestion by a subject. Compositions for oral use may be formulated, for example, in combination with a solid excipient, optionally grinding the resulting mixture, and processing the mixture of granules, after adding suitable additional compounds, if desired, to obtain tablets or dragee cores. Suitable excipients include carbohydrate or protein fillers. These include, but are not limited to, sugars, including lactose, sucrose, mannitol, or sorbitol, starch from corn, wheat, rice, potato, or other plants; cellulose such as methyl cellulose, hydroxypropylmethyl-cellulose, or sodium carboxymethyl-cellulose; and gums including arabic and tragacanth; as well as proteins, such as gelatin and collagen. If desired, disintegrating or solubilizing agents may be added, such as the crosslinked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage).

Compounds for oral administration may be formulated, for example, as push-fit capsules made of gelatin, as well as soft, sealed capsules made of gelatin and a coating such as glycerol or sorbitol. Push-fit capsules may contain the compounds mixed with filler or binders such as lactose or starches, lubricants such as talc or magnesium stearate, and, optionally, stabilizers. In soft capsules, the covalent conjugates may be dissolved or suspended in suitable liquids, such as fatty oils, liquid paraffin, or liquid polyethylene glycol with or without stabilizers.

For topical or nasal administration, penetrants appropriate to the particular barrier to be permeated are typically used in the formulation. Examples of these are 2-pyrrolidone, N-methyl-2-pyrrolidone, dimethylacetamide, dimethylformamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface-active agents. Keratolytic agents such as those known in the art may also be included. Examples are salicylic acid and sulfur. For topical administration, the composition may be in the form of a transdermal ointment or patch for systemic delivery of the compound and may be prepared in a conventional manner (see, e.g., Barry, Dermatological Formulations (Drugs and the Pharmaceutical Sciences—Dekker); Harry's Cosmeticology (Leonard Hill Books).

For rectal administration, the compositions may be administered in the form of suppositories or retention enemas. Such compositions may be prepared by mixing the compounds with a suitable non-irritating excipient that is solid at ordinary temperatures but liquid at the rectal temperature and will therefore melt in the rectum to release the drug. Suitable excipients include, but are not limited to, cocoa butter and polyethylene glycols.

The amounts of each of these various types of additives will be readily apparent to those skilled in the art, optimal amounts being the same as in other, known formulations designed for the same type of administration.

Compositions containing the compounds of the invention may be manufactured in a manner similar to that known in the art (e.g., by means of conventional mixing, dissolving, granulating, dragee-making, levigating, emulsifying, encapsulating, entrapping or lyophilizing processes). The compositions may also be modified to provide appropriate release characteristics, sustained release, or targeted release, by conventional means (e.g., coating). As noted above, in one embodiment, the compounds are formulated as an emulsion.

After compositions formulated to contain a compound and an acceptable carrier have been prepared, they can be placed in an appropriate container and labeled for use. Thus, in another aspect, the invention provides kits.

Lipophilic di(anticancer drug) compounds of the invention are suitable for administration as oil-in-water emulsions and micelle formulations. The compounds provide for high drug loading to enable small volumes for administration.

Emulsions containing lipophilic di(anticancer drug) compounds of the invention may provide for longer plasma half-life compared to conventional methods of drug compound administration resulting in prolonged exposure of targeted sites to the compounds. Lipophilic di(anticancer drug) compounds may also achieve high permeation through lipoidal membranes of targeted cells. Greater response without an increase in toxicity may be provided by the lipophilic di(anticancer drug) compounds of the invention as compared to unmodified parent compounds.

The following examples are provided to illustrate, not limit, the invention.

EXAMPLES

Example 1

The Preparation of a Representative Lipophilic Di(Anticancer Drug) Compound: Sebacate bis(7-ethylcamptothecin-10-yl)ester A mixture containing 196 mg (0.5 mmol) of 7-ethyl-10-hydroxycamptothecin, 51 mg (0.25 mmol) of sebacic acid, 128 mg (0.5 mmol) of 2-chloro-1-methylpyridinium iodide, 122 mg (1 mmol) of 4-(dimethylamino)pyridine, and 25 mL of N,N-dimethylformamide was stirred at room temperature overnight. The mixture was filtered, and the filtrate was concentrated to about 5 mL under reduced pressure. The crude product was then purified by column chromatography on silica gel (chloroform-methanol) to provide sebacate bis(7-ethylcamptothecin-10-yl)ester, 68 mg, 28.7%.

IR ($v_{max}$ cm$^{-1}$): 3303.03, 2925.01, 2867.67, 1749.25, 1659.00, 1598.38, 1556.79, 1509.37, 1460.94, 1414.50, 1376.89, 1306.83, 1226.71, 1155.73, 1107.40, 1052.28, 1032.45, 946.97, 918.77, 833.20, 807.82, 723.37, 665.93.

MS (Positive ESI): m/z 951.7=[M+H]$^+$ $^1$H NMR (300 MHz, CDCl$_3$): δ 7.994-7.963 (2H, d, J=9.3 Hz), 7.778-7.770 (2H, d, J=9.0 Hz), 7.501 (2H, s), 7.447-7.408 (2H, dd, J$_1$=9.0 Hz & J$_2$=2.4 Hz), 5.746-5.239 (4H, q, J$_1$=135.6 Hz & J$_2$=16.2 Hz), 5.239-5.215 (4H, m), 3.959 (2H, s), 3.184-3.109 (4H, q, J=7.2 Hz, 2.711-2.663 (4H, t, J=7.2 Hz), 1.926-1.913 (4H, m), 1.584-1.494 (12H, m), 1.453-1.402 (6H, t, J=7.5 Hz), 1.046-0.997 (6H, t, J=7.2 Hz).

Example 2

The Preparation of a Representative Lipophilic Di(Anticancer Drug) Compound: Sebacate bis(camptothecin-20-yl)ester A mixture containing 348 mg (1 mmol) of camptothecin, 101 mg (0.5 mmol) of sebacic acid, 224 mg (2 mmol) of 4-(dimethylamino)pyridine, 255 mg (1 mmol) of 2-chloro-1-methylpyridinium iodide, and 25 mL of N,N-dimethylformamide was stirred at room temperature overnight. The mixture was filtered, and the filtrate was concentrated to about 5 mL under reduced pressure. The crude product was then purified by column chromatography on silica gel (dichloromethane-methanol) to provide sebacate bis(camptothecin-20-yl)ester, 137 mg, 31.75%.

IR ($v_{max}$ cm$^{-1}$): 3431.01, 3066.48, 2926.31, 2855.52, 1737.99, 1669.41, 1625.82, 1563.93, 1500.07, 1458.41, 1440.80, 1405.54, 1366.40, 1351.94, 1323.55, 1296.42, 1247.50, 1231.54, 1204.22, 1166.65, 1151.98, 1131.89, 1086.02, 1045.80, 1019.49, 993.72, 946.00, 928.74, 913.78, 889.50, 876.77, 860.99, 827.71, 812.63, 786.59, 760.28, 722.77, 708.41, 654.22.

MS (Positive ESI): m/z 863.7=[M+H]$^+$ $^1$H NMR (300 MHz, CDCl$_3$): δ 8.379 (s, 2H), 8.211-8.184 (d, J=8.1 Hz, 2H), 7.944-7.919 (d, J=7.5 Hz, 2H), 7.854-7.798 (dt, J$_1$=6.9 Hz, J$_2$=1.2 Hz, 2H), 7.688-7.637 (t, J=7.5 Hz, 2H), 7.185 (s, 2H), 5.706-5.374 (ABq, J=17.1 Hz, 4H), 5.272 (s, 4H), 2.391-2.342 (t, J=7.2 Hz, 4H), 2.315-2.101 (m, 4H), 1.578-1.476 (m, 8H), 1.196 (bs, 4H), 0.988-0.938 (t, J=7.5 Hz, 6H).

Example 3

The Preparation of a Representative Lipophilic Di(Anticancer Drug) Compound: Sebacate bis(paclitaxel-2'-yl)ester A mixture containing 854 mg (1 mmol) of paclitaxel, 130 mg (0.5 mmol, 116 μl, 92%) of sebacoyl chloride, 121 mg (1.2 mmol, 167 μL) of triethylamine, and 100 mL of dichloromethane was stirred at room temperature overnight. The reaction mixture was washed with DI-water (3×100 mL), and dried over anhydrous magnesium sulfate. The crude product was purified by recrystallization in acetone and diethyl ether to provide sebacate bis(paclitaxel-2'-yl)ester, 664 mg, 70.86%.

IR ($v_{max}$ cm$^{-1}$): 3493.48, 2937.63, 1718.15, 1664.47, 1602.70, 1581.87, 1516.40, 1485.05, 1451.54, 1370.10, 1313.77, 1237.99, 1177.52, 1144.49, 1094.62, 1068.08, 1024.54, 979.03, 947.60, 905.77, 854.84, 800.35, 775.06, 708.36, 629.08, 604.43, 594.12, 580.97, 572.88, 566.13, 559.49, 551.82, 545.53, 535.83, 524.42.

MS (Positive ESI): m/z 1874.9=[M+H]$^+$ $^1$H NMR (300 MHz, CDCl$_3$): δ 8.148-8.119 (m, 4H), 7.739-7.710 (m, 4H), 7.639-7.590 (m, 2H), 7.543-7.7.474 (m, 6H), 7.7.436-7.7.307 (m, 14H), 6.916-6.885 (d, J=9.3 Hz, 2H), 6.297 (s, 2H), 6.275-6.219 (t, J=8.4 Hz, 2H), 5.969-5.928 (dd, J$_1$=9.0 Hz, J$_2$=3.3 Hz, 2H), 5.692-5.668 (d, J=7.2 Hz, 2H), 5.515-5.504 (d, J=3.3 Hz, 2H), 4.988-4.961 (m, 2H), 4.445 (m, 2H), 4.332-4.304 (d, J=8.4 Hz, 2H), 4.210-4.183 (d, J=8.1 Hz, 2H), 3.825-3.801 (d, J=7.2 Hz, 2H), 2.607-2.297 (m, 16H), 2.214 (s, 6H), 2.187-2.105 (m, 4H), 1.939 (s, 6H), 1.884-1.843 (m, 2H), 1.733 (s, 2H), 1.680-1.534 (m, 10H), 1.226-1.132 (m, 20H).

Example 4

The Preparation of a Representative Lipophilic Di(Anticancer Drug) Compound: Sebacate bis(docetaxel-2'-yl)ester A 100 mL flask was charged with 120 mg (108 μL, 0.5 mmol) of sebacoyl chloride (99%), 808 mg (1 mmol) of docetaxel, 134 mg (1.1 mmol) of 4-dimethylaminopyridine, 40 mL of anhydrous toluene and 10 mL of anhydrous acetonitrile. The mixture was stirred at room temperature overnight. The crude product was purified by column chromatography on silica gel to provide 716 mg of sebacate bis(docetaxel-2'-yl)ester. yield 80.36%.

IR ($v_{max}$ cm$^{-1}$): 3444.38, 3066.14, 2977.07, 2932.57, 1712.75, 1602.93, 1586.20, 1495.39, 1452.61, 1367.33, 1314.69, 1242.13, 1160.56, 1137.06, 1063.00, 1024.74, 983.01, 946.01, 916.37, 887.78, 851.81, 828.75, 801.51, 775.93, 755.96, 707.85

MS (Positive ESI): m/z 1872.3 (M+H)$^+$.

¹H NMR (300 MHz, CDCl₃): δ 8.122-8.098 (d, J=7.2 Hz, 4H), 7.639-7.590 (t, 2H), 7.531-7.481 (t, 4H), 7.410-7.274 (m, 10H), 6.223 (t, 2H), 5.692-5.669 (d, J=6.9 Hz, 2H), 5.419-5.377 (m, 6H), 5.212 (s, 2H), 4.981-4.954 (d, J=8.1 Hz, 2H), 4.337-4.176 (m, 8H), 3.937-3.914 (d, J=6.9 Hz, 2H), 2.638-2.534 (m, 2H), 2.429 (s, 6H), 2.389-2.277 (m, 6H), 2.172-2.148 (m, 2H), 1.939 (s, 6H), 1.892-1.808 (m, 2H), 1.747 (s, 6H), 1.664 (s, 2H), 1.534 (bs, 4H), 1.337 (s, 18H), 1.225 (s, 6H), 1.190 (bs, 8H), 1.120 (s, 6H).

Example 5

In Vitro Cytotoxicity of Representative Lipophilic Di(Anticancer Drug) Compound

In this example, the in vitro cytotoxicity, as measured by $GI_{50}$ (50% of growth inhibition) values, was determined for representative lipophilic di(anticancer drug) compounds of the invention. The $GI_{50}$ values of sebacate bis(7-ethylcamptothecin-10-yl)ester, sebacate bis(camptothecin-20-yl)ester, sebacate bis(paclitaxel-2'-yl)ester, and sebacate bis(docetaxel-2'-yl)ester, were measured in the following cancer cell lines: NCI-H460 (non-small cell lung), MDA-MB-231 (breast), HCT-166 (colon), and SKOV-3 (ovarian).

The study was performed using a solution of the lipophilic di(anticancer drug) compounds in DMSO (1 mM) diluted in the corresponding cell media. The cells were in contact with varying concentrations of the drug for a period of 48 hours. At the end of 48 hours, staining with Sulforhodamine B was performed to determine the number of viable cells and calculate the degree of cellular growth inhibition as compared to a control group. The calculated $GI_{50}$ values are shown in Table 1.

TABLE 1

Drug concentration that produces 50% cell growth inhibition ($GI_{50}$).

| Compound | Cell line | | | |
|---|---|---|---|---|
| | H460 (NSCLC) | MDA-MB-231 (BREAST) | HCT-116 COLON) | SKOV-3 (OVARIAN) |
| sebacate bis(7-ethylcampto-thecin-10-yl) | 3.03 nM | 302.68 nM | 4.58 nM | 8.53 nM |
| sebacate bis(camptothecin-20-yl)ester | 3.15 μM | 9.25 μM | 849.1 nM | 8.54 μM |
| sebacate bis(paclitaxel-2'-yl)ester | 83.18 nM | 84.30 nM | 39.85 nM | 40.18 nM |
| sebacate bis(docetaxel-2'-yl)ester | 16.67 nM | 110.64 nM | 20.87 nM | 135.09 nM |

While illustrative embodiments have been illustrated and described, it will be appreciated that various changes can be made therein without departing from the spirit and scope of the invention.

The invention claimed is:

1. A compound having the formula:

D-A-R'-A'-D wherein,
D is an anticancer drug moiety, wherein the anticancer drug is selected from the group consisting of paclitaxel, docetaxel, and derivatives thereof;
R' is a moiety selected from the group consisting of:
  (a) substituted and unsubstituted alkyl,
  (b) substituted and unsubstituted branched alkyl,
  (c) substituted and unsubstituted heteroalkyl,
  (d) substituted and unsubstituted cycloalkyl,
  (e) substituted and unsubstituted alkenyl,
  (f) substituted and unsubstituted alkynyl,
  (g) substituted and unsubstituted aryl, and
  (h) substituted and unsubstituted aralkyl;
A and A' are independently selected from the group consisting of:
  (a) —S(═O)—,
  (b) —SO₂—,
  (c) —SO(NR₁)—
  (d) —C(═O)—
  (e) —C(═O)O—,
  (f) —C(═O)NR₁—,
  (g) —C(═O)OC(═O)—,
  (h) —C(═O)OC(═O)O—,
  (i) —P(═O)(OR₁)O—,
  (j) —P(═O)(NR)O—,
  (k) —SO₂O—,
  (l) —S(═O)NR₁—,
  (m) —SO₂NR₁—,
  (n) —O—, and
  (o) —NHR₁—,
  wherein $R_1$ is selected from hydrogen, $C_{1-6}$ n-alkyl, $C_{3-12}$ branched alkyl, substituted or unsubstituted $C_{3-6}$ cycloalkyl, substituted or unsubstituted aryl, and substituted or unsubstituted aralkyl.

2. A compound of claim 1 selected from the group consisting of:
  (a) sebacate bis(paclitaxel-2'-yl) ester, and
  (b) sebacate bis(docetaxel-2'-yl) ester.

3. A compound of claim 1, wherein A-R'-A' is sebacate.

4. An emulsion, comprising:
  (a) an oil phase comprising
    (i) a compound of claim 1; and
    (ii) a lipophilic medium; and
  (b) an aqueous phase.

5. The emulsion of claim 4, wherein the lipophilic medium comprises a tocopherol.

6. A micelle formulation, comprising:
  (a) a compound of claim 1; and
  (b) an aqueous phase.

7. A method for treating non-small cell lung cancer, breast cancer, colon cancer, or ovarian cancer, comprising administering to a subject in need thereof a therapeutically effective amount of a compound of claim 1.

8. The method of claim 7, wherein administering the compound comprises administering an emulsion comprising the compound.

9. The method of claim 7, wherein administering the compound comprises administering a micelle formulation comprising the compound.

* * * * *